(12) United States Patent
Kaiser et al.

(10) Patent No.: US 10,179,197 B2
(45) Date of Patent: Jan. 15, 2019

(54) CATHETER PUMP WITH A PUMP HEAD FOR INSERTION INTO THE AORTA

(71) Applicant: CardioBridge GmbH, Hechingen (DE)

(72) Inventors: Siegfried Kaiser, Rottenburg/Hailfingen (DE); Klaus Epple, Rangendingen (DE)

(73) Assignee: CardioBridge GmbH, Hechingen (DE)

( * ) Notice: Subject to any disclaimer, the term of this patent is extended or adjusted under 35 U.S.C. 154(b) by 101 days.

(21) Appl. No.: 15/357,582

(22) Filed: Nov. 21, 2016

(65) Prior Publication Data

US 2018/0140759 A1 May 24, 2018

(51) Int. Cl.
*A61M 1/10* (2006.01)
*A61M 25/01* (2006.01)
*A61M 25/00* (2006.01)
*A61M 1/12* (2006.01)

(52) U.S. Cl.
CPC ........ *A61M 1/1024* (2014.02); *A61M 1/1012* (2014.02); *A61M 1/1034* (2014.02); *A61M 1/125* (2014.02); *A61M 25/0074* (2013.01); *A61M 25/01* (2013.01); *A61M 2205/025* (2013.01); *A61M 2205/0266* (2013.01)

(58) Field of Classification Search
CPC . A61M 1/1024; A61M 1/125; A61M 25/0074
See application file for complete search history.

(56) References Cited

U.S. PATENT DOCUMENTS

| | | | | |
|---|---|---|---|---|
| 5,749,855 A | * | 5/1998 | Reitan | A61M 1/1024 604/131 |
| 8,439,859 B2 | * | 5/2013 | Pfeffer | A61M 1/12 604/6.11 |
| 9,028,392 B2 | * | 5/2015 | Shifflette | A61M 1/101 600/16 |
| 9,089,634 B2 | * | 7/2015 | Schumacher | F04D 29/181 |
| 9,416,783 B2 | * | 8/2016 | Schumacher | F04D 3/00 |
| 9,416,791 B2 | * | 8/2016 | Toellner | F04D 29/18 |
| 9,895,475 B2 | * | 2/2018 | Toellner | A61M 1/12 |
| 2016/0022890 A1 | | 1/2016 | Schwammenthal et al. | |
| 2016/0136343 A1 | | 5/2016 | Anagnostopoulos | |
| 2016/0287771 A1 | | 10/2016 | Khanal et al. | |

FOREIGN PATENT DOCUMENTS

EP 0 768 900 B1 4/1997
EP 2 308 422 B1 4/2011

\* cited by examiner

*Primary Examiner* — Eric D. Bertram
(74) *Attorney, Agent, or Firm* — Aslan Law, P.C.

(57) ABSTRACT

A catheter pump comprising a pump head for insertion into the aorta. The pump head includes: a rotor having propellers that can be displaced from a folded insertion position in which the pump head can be inserted into the aorta, to an unfolded operating position in which the rotor can be set in rotation, and a cage surrounding the propellers. The cage comprises a distal, proximal sheath and filaments running between sheaths. The sheaths are moved towards one another at or before the unfolding of the propellers in a manner that the regions of the filaments lying between the sheaths expand radially outward, to form a space surrounding the unfolded propellers. At least some or all of the filaments are configured so as to each have at least one main section that engages one sheath and splits into at least two minor sections in the direction toward the other sheath.

13 Claims, 3 Drawing Sheets

CATHETER PUMP WITH A PUMP HEAD FOR INSERTION INTO THE AORTA

The present invention relates to a catheter pump comprising a pump head for insertion into the aorta, in particular, into the aorta of a human, comprising a rotor having propellers that can be displaced from a folded insertion position in which the pump head can be inserted into the aorta, to an unfolded operating position in which the rotor can be set in rotation. Further provided is a cage that surrounds the propellers and comprises a distal sheath, a proximal sheath, and filaments running between the sheaths. The sheaths are then arranged so as to be moved towards one another at or before the unfolding of the propellers in such a manner that the regions of the filaments lying between the sheaths expand radially outward, in order to form a space surrounding the unfolded propellers.

A catheter pump comprising such a pump head is disclosed, for example, in EP 0 768 900 B1 and EP 2 308 422 B1. The propellers are then set in rotation by a drive shaft that lies within a catheter. The movement of the sheaths toward one another or away from one another—and thus the expansion or compression of the cage—takes place via an axial displacement of an inner catheter relative to an outer catheter, and via a concomitant axial displacement of the proximal sheath.

In the known prior art, the filaments between the sheaths are constituted of bands or strips that run in the axial direction and have predetermined bending points.

When such catheter pump heads are being operated, i.e., when the cage is in the expanded state, the filaments regularly come into contact with the vascular wall. It has been shown that the contact made between the filaments and the inner vascular wall may lead to undesired vascular damage (trauma to the vascular wall). It has also been discovered that, due to the forces acting thereon, the filaments of the cages of the known catheter pump heads tend to be laterally deflected.

The present invention addresses the problem of proposing a catheter pump that remedies the aforementioned disadvantages. This problem is solved by a catheter pump having the features of claim 1.

The catheter pump according to the present invention is therefore characterized in particular in that some or all of the filaments are configured so as to each have at least one main section that engages one sheath and splits into at least two minor sections in the direction toward the other sheath. The splitting of the main section into a plurality of minor sections makes it possible to achieve a greater stability of the cage, in particular the expanded cage. Overall, this allows both lateral and higher forces to act on the cage, without the cage being unintentionally deformed and without the individual filaments being unintentionally laterally deflected. The main section can then be split into the minor sections, in particular, in an Y-shaped manner, resulting in suitable stability.

The splitting of the main sections into the minor sections also has an advantage in that, optionally additional catheters to be inserted into the aorta can be safely introduced past the pump head. These additional catheters may then come to bear, for example, against the Y-shaped splits on the side facing away from the main section. Proper placement of the Y-shaped split can prevent an overly close approach of the additional catheter to the rotating propellers.

It is advantageous when the main section extends over ⅕ to ⅖ of the length and preferably over a range of ¼ to ⅓ of the respective filament. On uniform expansion of the individual filaments, this makes it possible to have it be not the main section but rather the minor sections that come to bear against the vascular wall. Because the main sections split into minor sections, the pressing force of the cage or the filaments thereof against the inner vascular wall is distributed across the plurality of minor sections. Because overall there are more minor sections than main sections provided, the pressing forces are better distributed and are thus lower in the minor sections than in the pre-existing prior art, which has only main sections. The risk of vascular damage (trauma) is lowered due to the lower pressing forces against the vascular wall. Overall, this makes it possible to achieve atraumatic—i.e., tissue-protecting-action. It is advantageous when the minor sections extend at least over the middle regions of the filaments, because the middle regions of the filaments tend to come to bear against the inner vascular wall during operation of the catheter head. In addition, suitable selection of the length of the main sections makes it possible to prevent an additional catheter guided past the pump head from coming too close to the rotating propellers.

It is further advantageous when the cross-sectional area of the respective main section is greater than the cross-sectional area of one corresponding minor section. This, too, makes it possible to achieve an atraumatic action.

It has been found to be advantageous when the cross-sectional area of the main section essentially corresponds to the sum of the cross-sectional areas of the minor sections. When, for example, there are two minor sections provided, the cross-sectional areas thereof may correspond to the cross-sectional area of the main section. To implement the minor sections, for example, a main section may be split down the middle into two minor sections.

Another especially preferred cage arises when two minor sections of main sections that are adjacently engageable with one sheath each unite in the direction toward the other sheath into one main section that engages with the respective other sheath. The main section, starting from one sheath, consequently divides toward the other sheath into two minor sections. The two adjacent minor sections of different main sections each then further unite into one main section, which engages the other sheath. This results in a suitable, symmetrical arrangement with which, in particular, the filaments of only minor sections are provided in the middle region between the sheaths, and only main sections are provided in the regions near the sheaths. Another result is a comparatively high stability, because the minor sections are then configured as braches between adjacent main sections each engaging tho other sheath.

The arrangement of the main sections is furthermore advantageous in that the main sections engaging one sheath lie in axial extension, in particular, centrally between two adjacent main sections engaging the other sheath. In side view, a main section engaging one sheath always lies between two main sections that engage another sheath.

In order to achieve sufficient and defined expansion of the filaments, it is advantageous when the filaments between the main sections and the respective sheaths have a transitional section having a reduced cross-sectional area. This ensures that the filaments assume a designated position when the sheaths are moved to one another.

A nickel-titanium alloy has proven especially advantageous as material for the cage. Such alloys have the necessary superelastic properties and provide the required durability to ensure a safe cage. The cage may also, however, be produced from a plastic material having corresponding properties.

The pump head is then preferably arranged in the region of a free end of a catheter. The catheter preferably has a drive shaft—which is arranged so as to be rotatably mounted in the catheter—in order to drive the rotor and a drive in order to drive the drive shaft. The drive is then advantageously arranged on the side of the drive shaft that faces away from the pump head.

The following description sets forth further details of advantageous configurations of the present invention, by which an embodiment of the present invention is described and explained in greater detail.

Figure 1:
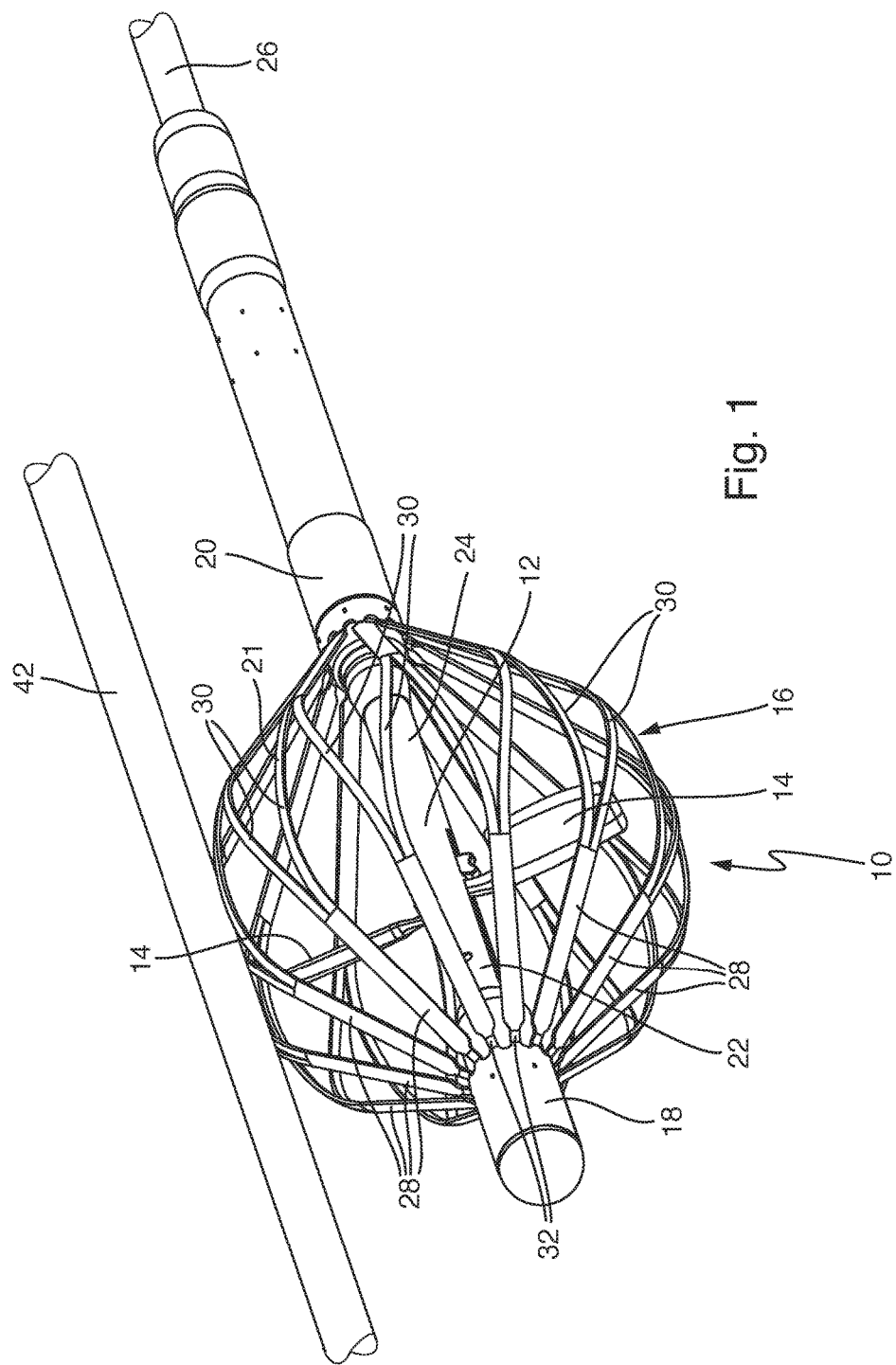
FIG. 1 illustrates the pump head of a catheter pump according to the present invention in the operating position.

The pump head 10 illustrated in the drawings comprises a rotor 12 with two propellers 14. Further provided is a cage 16 that surrounds the rotor 12 and comprises a distal sheath 18, a proximal sheath 20, and filaments 21 running between the sheaths.

The rotor 12 is movably connected via a shaft section 22 to the distal sheath 18 in the axial direction. The rotor 12 is movably connected—via a drive shaft 24 that is arranged so as to be able to rotate within an outer catheter 26 and so as to be displaceable in the axial direction—at the side facing away from the sheath 18.

The pump head 10 illustrated in FIG. 1 is in the operating position, in which both propellers 14 are unfolded.

To introduce the pump head 10 into the aorta, the two sheaths 18, 20 are in a position of separation from one another, in which the propellers 14 are folded and the filaments 21 abut closely against the rotor 12 or against the shaft section 22 and the drive shaft 24.

To expand the cage 16, the section of the drive shaft 24 adjacent to the rotor 20 is moved into the outer catheter 26, whereby the sheath 18 is moved toward the sheath 20. In this first step, the filaments 21 of the cage 16 expand radially outward. On further displacement of the sheath 18 toward the sheath 20, the propellers 14 of the rotor 12 fold into the operating position, as illustrated in FIG. 1.

Figure 2:
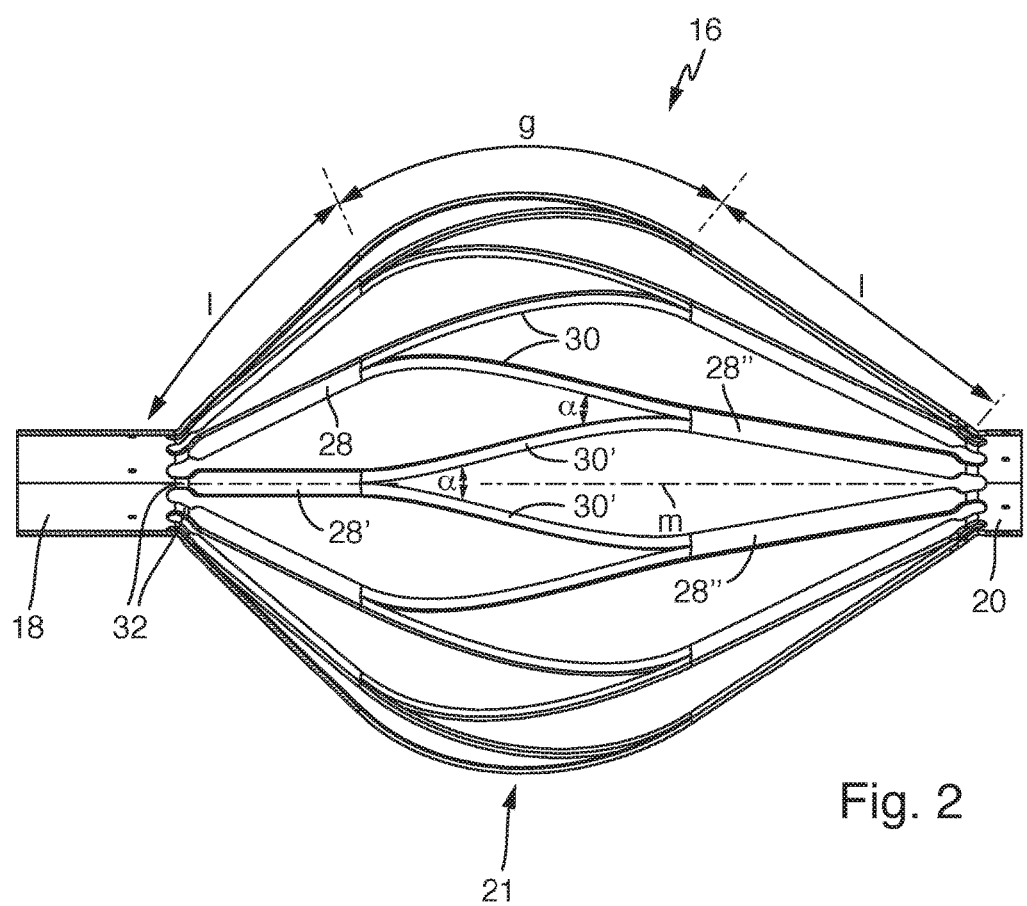
FIG. 2 illustrates a longitudinal section, through the cage, of the pump head according to FIG. 1 in the operating position.

As is clear from FIGS. 1 and 2, the filaments 21 are configured so as to each have a main section 28 that engages one sheath 18, 20 and splits into two minor sections (30) in the shape of a Y in the direction toward the other sheath 18, 20. The two minor sections 30 then, when in the operating position, lock in an angle α of about 15° to 35°, in particular, in the area of 30°. The main sections 28 extend over a length l. In the embodiment depicted, the length l amounts to about ⅓ the total length of the respective filament 21. The minor sections 30 then extend over the middle region of the filaments 21 and have a length g, which also occupy about ⅓ the total length of the filaments 21. The selection of the lengths l and g makes it possible to achieve a certain rising behavior or a certain cage diameter. Respectively different values then arise for the angle α.

The cross-sectional area of a main section 28 is approximately twice as large as the cross-sectional area of the minor sections 30 adjoining that main section 28.

As is clear, in particular, from FIG. 2, two minor sections 30, 30' of adjacent main sections 30, 30' engaging one sheath 18, 20 each unite toward the other sheath 20, 18 into a common main section 28". The minor sections 30, 30' overall thereby form bracco between adjacent main sections 28, 28'.

The main sections 28 engaging one sheath 20, 18 are then arranged so as to be offset in the axial direction to the main sections 28 that engage the other sheath 18, 20. The main sections 28 at one sheath 20, 18 are preferably centrally located between the main sections 28 that engage the other sheath 18, 20. This is shown in FIG. 2 by a line m that depicts the axis of the main section 28' that engages the sheath 18. The line m is centrally located between the main sections 28" that engage the sheath 20.

Figure 3:
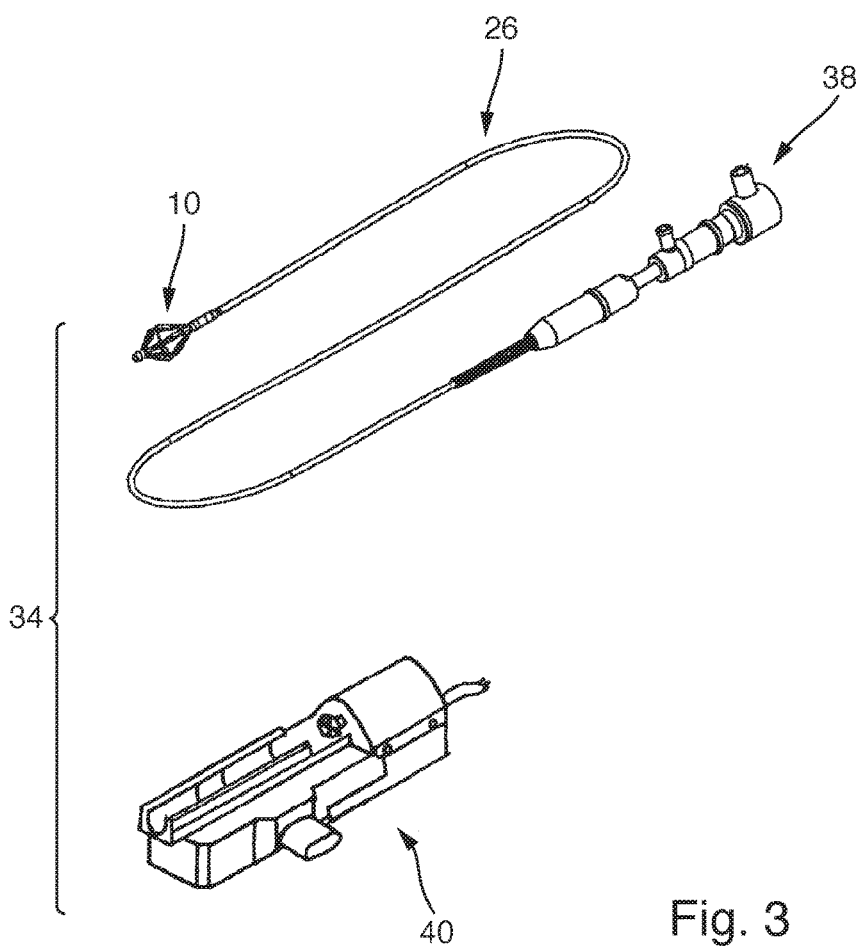
FIG. 3 illustrates a catheter pump according to the present invention comprising a pump head according to FIG. 1.

The arrangement and design of the filaments 21 such as illustrated in FIGS. 1 to 3 achieves, on the one hand, a more uniform distribution of the forces acting on the inner wall of the vessel during the operation of the catheter pump 34. The load on the vascular wall overall is thereby reduced. On the other hand, the cage 16 develops very high stability with still-sufficient flow characteristics for the blood to be conveyed.

Moreover, an additional catheter 42, illustrated in FIG. 1, can be guided through the vessel past the catheter 26 and past the pump head 10, without this additional catheter 42 impairing the function of the pump head 10 and the rotating propellers 14. The additional catheter 42 is then guided between the minor sections 30 and cannot enter into the rotation region of the propellers 14 due to the main sections 28 adjoining the minor sections 30.

FIGS. 1 and 2 also make clear that the filaments 21 between the main sections 28 and the sheaths 18, 20 each have a transitional section 32 that has a reduced cross-sectional area in relation to the main section. This makes it possible to achieve favorable elastic properties of the filaments 21 in the region of the sheaths 18 and 20.

FIG. 3 illustrates a catheter pump 34 according to the present invention, which has a pump head 10 according to the present invention that is provided in the region of a free end of the catheter 26. The drive shaft 24, by means of which the rotor 12 can be set in rotation, is provided in the catheter 26. At the end facing away from the pump head 10, the catheter 26 provides for a drive section 38 that can be inserted into a drive unit 40 by means of which ultimately the drive shaft 24—and the rotor 12 therewith—can be set in rotation.

The invention claimed is:

1. A catheter pump comprising a pump head for insertion into the aorta, wherein the pump head includes: a rotor having propellers that can be displaced from a folded insertion position in which the pump head can be inserted into the aorta, to an unfolded operating position in which the rotor can be set in rotation, and a cage surrounding the propellers, wherein the cage comprises a distal, proximal sheath and filaments running between the sheaths, and wherein the sheaths are moved towards one another at or before the unfolding of the propellers in such a manner that the regions of the filaments lying between the sheaths expand radially outward, in order to form a space surrounding the unfolded propellers, wherein at least some or all of the filaments are configured so as to each have at least one main section that engages one sheath and splits into at least two minor sections in the direction toward the other sheath, wherein two minor sections of main sections that are adjacently engageable with one sheath each unite in the direction toward the other sheath into one main section that engages with the respective other sheath, wherein the sheaths include a first sheath and a second sheath, wherein a first minor section of a first main section of the first sheath is directly connected to only a first main section of the second sheath, and wherein a second minor section of the first main section of the first sheath is directly connected to only a second main section of the second sheath.

2. The catheter pump according to claim 1, wherein the respective main section extends over a range of ⅕ to ⅖ and over a range of ¼ to ⅓ of the length of the respective filament.

3. The catheter pump according to claim 2, wherein the selection of the length of the respective main section defines the opened cage diameter and the shape of the cage.

4. The catheter pump according to claim 2, wherein the length of the respective main section is selected so that an additional catheter can be guided past the pump head without the rotating propellers coming into contact with the additional catheter.

5. The catheter pump according to claim 4, wherein the minor sections extend over at least the middle regions of the filaments.

6. The catheter pump according to claim 5, wherein the cross-sectional area of one main section is greater than the cross-sectional area of one corresponding minor section.

7. The catheter pump according to claim 6, wherein the cross-sectional area of the main section corresponds at least largely to the sum of the cross-sectional areas of the minor sections.

8. The catheter pump according to claim 7, wherein the main sections engaging one sheath lie in axial extension between two adjacent main sections engaging the other sheath.

9. The catheter pump according to claim 8, wherein the filaments between the main sections and the respective sheaths have a transitional section having a reduced cross-sectional area.

10. The catheter pump according to claim 9, wherein the cage is composed of a resilient material.

11. The catheter pump according to claim 10, comprising a drive shaft provided in the catheter in order to drive the rotor and a drive for driving the drive shaft.

12. The catheter pump according to claim 10, wherein the resilient material is a nickel-titanium alloy.

13. The catheter pump according to claim 9, wherein the cage is composed of a plastic having corresponding properties.

* * * * *